(12) United States Patent
Roessl et al.

(10) Patent No.: US 8,213,566 B2
(45) Date of Patent: Jul. 3, 2012

(54) K-EDGE IMAGING

(75) Inventors: Ewald Roessl, Ellerau (DE); Roland Proksa, Hamburg (DE); Jens-Peter Schlomka, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/000,371

(22) PCT Filed: Jun. 22, 2009

(86) PCT No.: PCT/IB2009/052670
§ 371 (c)(1),
(2), (4) Date: Dec. 21, 2010

(87) PCT Pub. No.: WO2010/004460
PCT Pub. Date: Jan. 14, 2010

(65) Prior Publication Data
US 2011/0096905 A1    Apr. 28, 2011

Related U.S. Application Data

(60) Provisional application No. 61/078,575, filed on Jul. 7, 2008.

(51) Int. Cl.
*A61B 6/00* (2006.01)
*G06K 9/00* (2006.01)

(52) U.S. Cl. .............. 378/5; 382/128; 382/131

(58) Field of Classification Search .......... 378/5, 98.9, 378/62; 382/128, 131
See application file for complete search history.

(56) References Cited

U.S. PATENT DOCUMENTS

| 3,848,130 | A | * | 11/1974 | Macovski | 378/98.9 |
| 3,974,386 | A | * | 8/1976 | Mistretta et al. | 378/98.11 |
| 4,029,963 | A | * | 6/1977 | Alvarez et al. | 378/5 |
| 4,686,695 | A | * | 8/1987 | Macovski | 378/146 |
| 4,788,706 | A | * | 11/1988 | Jacobson | 378/207 |
| 5,458,869 | A | | 10/1995 | Berg et al. | |
| 5,817,289 | A | | 10/1998 | Klaveness et al. | |

(Continued)

FOREIGN PATENT DOCUMENTS
WO   9316375 A1   8/1993
(Continued)

OTHER PUBLICATIONS

Firsching, M., et al.; A Method for Stoichiometric Material Reconstruction with Spectroscopic X-ray Pixel Detectors; 2004; IEEE Nuclear Science Symposium Conference Record; vol. 7; pp. 4116-4119.

(Continued)

*Primary Examiner* — Alexander H Taningco

(57) ABSTRACT

An imaging system including a radiation source (110) that emits poly-chromatic radiation that traverses an examination region and a detector (116) that detects radiation traversing the examination region and produces a signal indicative of the energy of a detected photon. The system further includes an energy discriminator (122) that energy resolves the signal based on a plurality of different energy thresholds, wherein at least two of the energy thresholds have values corresponding to at least two different K-edge energies of two different elements in a mixture disposed in the examination region. The system also includes a signal decomposer (132) that decomposes the energy-resolved signal into at least a multi K-edge component representing the at least two different K-edge energies. In one instance, a stoichiometric ratio of the two different elements in the contrast agent is known and substantially constant.

17 Claims, 4 Drawing Sheets

U.S. PATENT DOCUMENTS

| | | | |
|---|---|---|---|
| 6,813,333 B2 * | 11/2004 | Karau et al. | 378/4 |
| 6,904,118 B2 * | 6/2005 | Wu et al. | 378/5 |
| 7,627,080 B2 * | 12/2009 | Proksa | 378/6 |
| 7,778,454 B2 * | 8/2010 | Grasruck et al. | 382/128 |
| 2005/0084060 A1 * | 4/2005 | Seppi et al. | 378/5 |
| 2008/0137803 A1 * | 6/2008 | Wu et al. | 378/5 |

FOREIGN PATENT DOCUMENTS

| | | | |
|---|---|---|---|
| WO | 2005051435 | A2 | 6/2005 |
| WO | 2006084382 | A1 | 8/2006 |
| WO | 2007055995 | A2 | 5/2007 |
| WO | 2008078231 | A1 | 7/2008 |
| WO | 2008078255 | A2 | 7/2008 |

OTHER PUBLICATIONS

Roessl, E., et al.; K-edge imaging in x-ray computed tomography using multi-bin photon counting detectors; 2007; Phys. Med. Biol.; 52:4679-4696.

Schlomka, J. P., et al.; Experimental feasibility of multi-energy photon-counting K-edge imaging in pre-clinical computed tomography; 2008; Phys. Med. Biol.; 53:4031-4047.

* cited by examiner

K-EDGE IMAGING

CROSS REFERENCE TO RELATED APPLICATIONS

This application claims the benefit of U.S. provisional application Ser. No. 61/078,575 filed Jul. 7, 2008, which is incorporated herein by reference.

The following generally relates to K-edge imaging. While it is described with particular application to computed tomography (CT), it also relates to other medical imaging and non-medical imaging applications.

A conventional computed tomography (CT) scanner includes an x-ray tube mounted on a rotatable gantry opposite one or more detectors. The x-ray tube rotates around an examination region located between the x-ray tube and the one or more detectors and emits polychromatic radiation that traverses the examination region and a subject and/or object disposed in the examination region. The one or more detectors detect radiation that traverses the examination region and generate a signal or projection data indicative of the examination region and the subject and/or object disposed therein. The projection data is used to reconstruct volumetric image data thereof, and the volumetric data can be used to generate one or more images of the subject and/or object. The resulting image(s) includes pixels that typically are represented in terms of grey scale values corresponding to relative radiodensity.

The grey scale values reflect the attenuation characteristics of the scanned subject and/or object, and generally show structure such as anatomical structures within a patient, physical structures within an inanimate object, and the like. However, since the absorption of a photon by a material is dependent on the energy of the photon traversing the material, the detected radiation also includes spectral information, which provides additional information such as information indicative of the elemental or material composition (e.g., atomic number) of the tissue and/or material of the subject and/or object. Unfortunately, conventional CT projection data does not reflect the spectral characteristics as the signal output by the one or more detectors as proportional to the energy fluence integrated over the energy spectrum. In spectral CT, the spectral characteristics are leveraged to provide further information such as information indicative of elemental composition.

A spectral CT system may include an energy resolving photon counting detector such as a direct conversion CZT detector (or CdTe, Si, GaAs, etc) that produces an electrical signal for each photon that it detects, wherein the electrical signal is indicative of the energy of that photon. A pulse shaper processes the signal and produces a voltage or current pulse with the peak amplitude indicative of the energy of the detected photon. A discriminator compares the amplitude of the pulse with one or more thresholds that are set in accordance with different energy levels. A counter counts, for each threshold, the number of times the amplitude exceeds the threshold. A binner bins or assigns a detected photon to an energy window based on the counts. The resulting energy-resolved detected photons provide information that can be used for spectral reconstruction of the signals for the detected photons.

K-edge imaging leverages the fact that high-Z elements tend to attenuate photons to a much higher extent above a particular energy, the K-edge energy of the given element, relative to attenuating photons just below the K-edge energy. The discontinuity in the attenuation behaviour of the element can be detected using an energy resolving photon counting detector such as the one noted above. Generally, since the K-edge of iodine is located at a rather low energy of around 33 keV, iodine is not well suited for K-edge imaging when the total attenuation is large and the x-ray spectrum is hardened considerably upon passage through the patient. One way to improve the sensitivity is to use an element with higher Z than iodine such as gadolinium, which has a K-edge at around 50 keV. Beam hardening at this energy is much less important and yields relative good results even for high attenuation.

However, there is an unresolved need to further improve the sensitivity in K-edge imaging.

Aspects of the present application address the above-referenced matters and others.

According to one aspect, an imaging system includes a radiation source that emits poly-chromatic radiation that traverses an examination region and a detector that detects radiation traversing the examination region and produces a signal indicative of the energy of a detected photon. The system further includes an energy discriminator that energy resolves the signal based on a plurality of different energy thresholds, wherein at least two of the energy thresholds have values corresponding to at least two different K-edge energies of two different elements in a mixture disposed in the examination region. The system also includes a signal decomposer that decomposes the energy-resolved signal into at least a multi K-edge component representing the at least two different K-edge energies.

In another aspect, a method includes detecting poly-chromatic radiation emitted by a radiation source that traverses an examination region and generating a signal indicative of the energy of a detected photon. The method further includes energy-resolving the signal based on a plurality of different energy thresholds, wherein at least two of the energy thresholds have values corresponding to at least two different K-edge energies of two different elements of a mixture disposed in the examination region, wherein a stoichiometric ratio of the two different elements of the mixture is known. The method further includes decomposing the energy-resolved signal into at least a multi K-edge component representing the at least two different K-edge energies. The method further includes reconstructing a multi K-edge image based on the multi K-edge component and the stoichiometric ratio to generate volumetric image data indicative of the two different elements.

In another aspect, a computer readable storage medium containing instructions which, when executed by a computer, cause the computer to perform the steps of: detecting polychromatic radiation traversing the examination region; producing a signal indicative of an energy of a detected photon; energy discriminating the signal based on a plurality of different energy thresholds, wherein at least two of the energy thresholds have values corresponding to at least two different K-edge energies of two different elements disposed in the examination region; and decomposing the energy-resolved signal into a multi K-edge component representing the at least two different K-edge energies.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 illustrates an imaging system.
FIG. 2 illustrates an example pulse energy discriminator.
FIG. 3 illustrates an example component decomposer.

Figure 1:
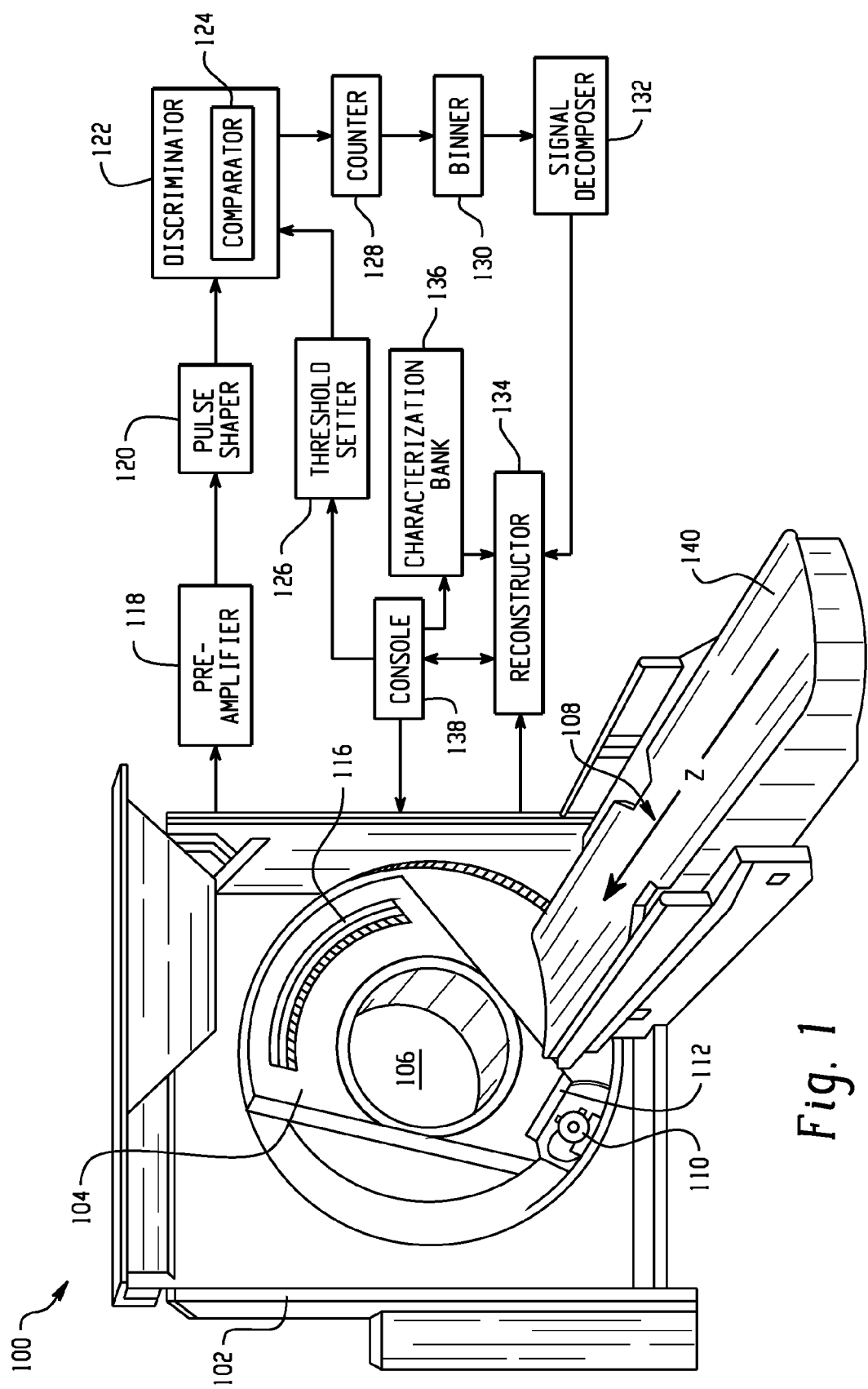

With reference to FIG. 1, a computed tomography (CT) system 100 includes a generally stationary gantry 102 and a rotating gantry 104, which is rotabably supported by the stationary gantry 102. The rotating gantry 104 rotates around an examination region 106 about a longitudinal or z-axis 108. An x-ray source 110, such as an x-ray tube, is supported by the rotating gantry 104 and emits poly-energetic radiation. A collimator 112 collimates the radiation beam to produce a generally cone, fan, wedge or other shaped radiation beam that traverses the examination region 106.

A radiation sensitive detector array 116 detects photons that traverse the examination region 106. The illustrated detector 116 is an energy-resolving detector such as a direct conversion detector (e.g., Si, Ge, GaAs, CdTe, CdZnTe, etc.) or a scintillator-based detector that includes a scintillator in optical communication with a photosensor. The detector 116 generates an electrical signal, such as electrical currents or voltages, for each detected photon.

A pre-amplifier 118 amplifies the electrical signal output by the detector 116. A pulse shaper 120 processes the amplified electrical signal and generates a pulse such as voltage or other pulse indicative of the energy of the detected photon. An energy discriminator 122 energy discriminates the pulse. In the illustrated example, the energy discriminator 122 includes a comparator 124 that compares the amplitude of the pulse with two or more different energy thresholds, which correspond to different energies of interest. The comparator 124 produces an output signal indicative of the energy of the photon based on the comparison.

A threshold setter 126 sets the thresholds. As described in greater detail below, the threshold setter 126 may be used to set two or more of the thresholds in accordance with the K-edge energies of elements of interest, such as different contrast elements in a contrast agent administered to a patient to be scanned. Using two or more thresholds tuned to the K-edges of two or more different Z elements in a given contrast agent may increase the sensitivity of the K-edge imaging technique. As such, when the system 100 is configured with tuneable thresholds, it may be desirable to tune the thresholds to the K-edge energies. Of course, thresholds may also be set to distinguish between Compton effect and photo-electric effect components.

A counter 128 increments a count value for each threshold based on the output of the energy discriminator 122. For instance, when the output of the comparator 124 for a particular threshold indicates that the amplitude of the pulse exceeds the corresponding threshold, the count value for that threshold is incremented. A binner 130 energy bins the signals and, hence, the photons into two or more energy bins based on the counts. An energy bin encompasses an energy range or window. For example, a bin may be defined for the energy range between two thresholds, where a photon resulting in a count for the lower threshold but not for higher threshold would be assigned to that bin.

A signal decomposer 132 decomposes the energy-resolved signals into various energy dependent components. For example, in one instance a detected energy-resolved signal is decomposed into a Compton component, a photo-electric component, and a multi K-edge component representative of two or more K-edge materials in a contrast agent. It is to be appreciated that a maximum likelihood or another decomposition technique may alternatively be used.

A reconstructor 134 selectively reconstructs the detected signals. In one instance, this includes reconstructing the Compton, photo-electric, and/or multi K-edge components, individually or in combination. For the multi K-edge component, the stoichiometric ratio of the contrast elements in the contrast agent should be known and constant in order to characterize the attenuation of the elements as a function of energy.

A characterization bank 136 includes information that characterizes the elements contributing to the multi K-edge component as such. This information may include a K-edge energy of the two or more elements, the stoichiometric ratio of the elements, etc. Such information is used when reconstructing the multi K-edge component as described in greater detail below.

A general purpose computer serves as an operator console 138. The console 138 includes a human readable output device such as a monitor or display and an input device such as a keyboard and mouse. Software resident on the console 138 allows the operator to interact with the scanner 100 via a graphical user interface (GUI) or otherwise.

Such interaction may include selecting a scan protocol such as a multi K-edge imaging protocol, setting an energy-discriminating threshold, etc.

An object support 140 such as a couch supports a patient or other object in the examination region 106. The object support 140 is movable so as to guide the object with respect to the examination region 106 for performing a scanning procedure.

As briefly discussed above, the scanner 100 may be used for multi K-edge component imaging of at least two different contrast elements in a contrast agent in a subject or object where the stoichiometric ratio of the elements is known and constant. With such an application, at least two of the thresholds of the comparator 124 are set in accordance with the K-edge energies of the at least two different contrast elements. The following describes an example for a contrast agent that includes both iodine and gadolinium for explanatory purposes and sake of brevity. It is to be understood that other contrast agents including the same or more and/or similar or different contrast materials are also contemplated herein.

Figure 2:
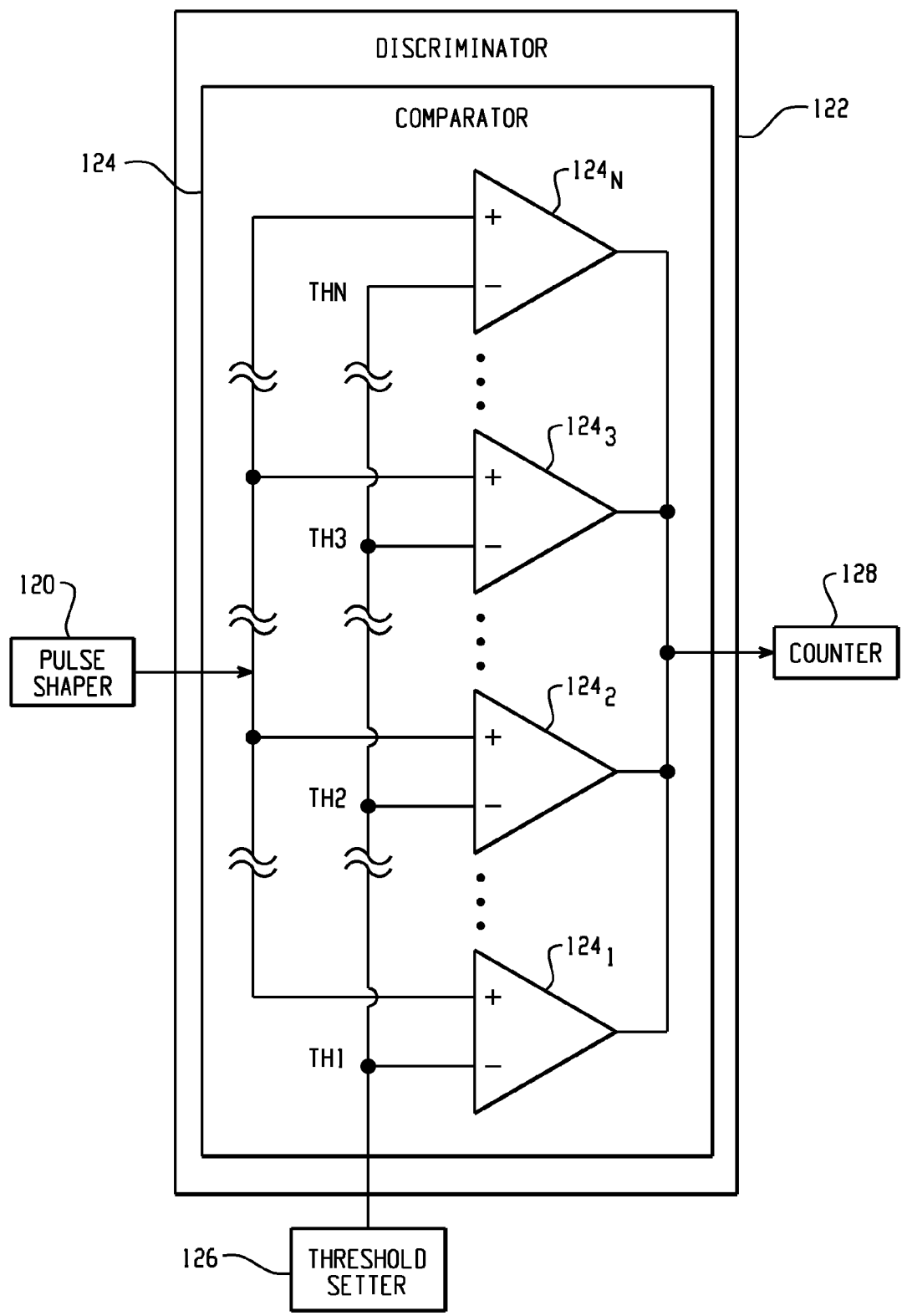

FIG. 2 illustrates a non-limiting example of the comparator 124 with two thresholds set in accordance with two different K-edge energies for two different elements in a contrast agent. As illustrated, the comparator 124 includes N sub-comparators $124_1, \ldots, 124_2, \ldots, 124_3, \ldots, 124_N$, wherein N is an integer equal to or greater than four. Each of the sub-comparators 124 includes a first input, which receives the output of the pulse shaper 120. Each of the comparators 124 also includes a second input, which receives a corresponding threshold value $TH_1, \ldots TH_2, \ldots TH_3, \ldots, TH_N$.

In this example, two of the thresholds are respectively set based on the K-edge energies of iodine (K-edge≈33 keV) and gadolinium (K-edge≈50 keV). Two other thresholds are set to distinguish between the Compton effect and the photo-electric effect. Where more or different elements having a desired K-edge are present in the contrast, one or more other thresholds may be set accordingly. For example, where the contrast agent includes Gold (K-edge≈80 keV), a threshold can be set accordingly. Generally, the K-edge energies should fall within the diagnostic imaging range of about 25 keV to about 150 keV. In one instance, the threshold setter 126 sets at least one of the thresholds based on a selected scan protocol. In another instance, an operator uses the threshold setter 126 to set at least one of the thresholds.

For each of the comparators $124_1, \ldots, 124_2, \ldots, 124_3, \ldots, 124_N$, when the amplitude of the incoming pulse exceeds the corresponding threshold, the output of the comparator $124_1, \ldots, 124_2, \ldots, 124_3, \ldots, 124_N$ changes state, for example, goes from low to high, 0 to 1, or other transition. The output of the comparator 124 is fed to the counter 128, which increments a count for each threshold based on a state transition.

Figure 3:
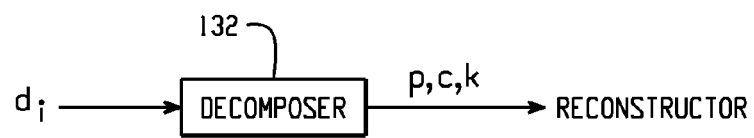

FIG. 3 illustrates an example signal decomposer 132. The following provides an example for the four threshold case, which includes two thresholds that can be used to distinguish between the Compton effect and the photo-electric effect, a threshold for a first K-edge energy and a threshold for a second K-edge energy. In this example, the signal decomposer 132 receives at least three energy-resolved detection signals $d_i$, wherein i is an integer, for the different energy bins. The detection signal $d_i$ shows a spectral sensitivity $D_1$ (E) of the i-th energy bin $b_i$. Furthermore, the emission spectrum T (E) of the polychromatic radiation source 110 is generally known.

The signal decomposer 132 models the information as a combination of the photo-electric effect with spectrum P(E), the Compton effect with spectrum C(E) and the multi K-edge contrast agent with spectrum K(E). The density length product for each of the components, in particular the photo-effect component p, the Compton-effect component c and the multi K-edge component k, in each detection signal $d_1$ is modeled in a discrete system in accordance with Equation 1:

$$d_n = \int dE\, T(E) D_n(E) \exp(-(p\, P(E) + c\, C(E) + k\, K(E))). \quad \text{Equation 1}$$

Since at least three detection signals $d_1$, $d_2$ and $d_3$ are available for the at least three energy bins $b_1$, $b_2$ and $b_3$, a system of at least three equations is formed having three unknowns, which can thus be solved with known numerical methods. Generally, three energy bins are sufficient in this case. However, using more detection signals for more energy bins may increase the sensitivity and noise robustness. If more than three energy bins are available, a maximum likelihood approach that takes into account the noise statistics of the measurements may be used. A suitable maximum likelihood approach is described in connection with "K-edge imaging in x-ray computed tomography using multi-bin photon counting detectors," E. Roessl and R. Proksa, 2007 Phys. Med. Biol. 52 4679-4696.

The results, in particular the components p, c and k, can then be used in order to reconstruct a desired component image with conventional reconstruction methods, in particular for reconstructing a multi K-edge component image. A conventional CT image as well as a Compton component image and/or a photo-electric component image may also be reconstructed.

When the stoichiometric ratio of the elements in the contrast agent is unknown, Equation 1 can be modified to include a K-edge component for each K-edge, for instance, one for Iodine, one for Gadolinium, etc. A suitable decomposition for the individual K-edge components is described in application serial number PCT/IB2007/055105, filed on Dec. 14, 2007, which claims the benefit of provisional application serial number EP 06126653.2, filed on Dec. 20, 2006, both of which are incorporated in their entirety herein by reference.

When the stoichiometric ratio of the elements in the contrast agent is known and substantially constant, the stoichiometric ratio of the elements in the contrast agent, along with K-edge energies thereof, characterizes the attenuation of the combination of the elements as a function of energy. As a consequence, the stoichiometric ratio and K-edge energies are used during reconstruction to generate a multi K-edge component image. The stoichiometric ratio and K-edge energy information can be stored in the characterization bank 136 for use by the reconstructor 134.

Generally, the stoichiometric ratio and K-edge energies provide a unique signature or fingerprint for the combination of elements. This is illustrated in connection with FIG. 4, which shows an attenuation curve 400 as a function of photon energy for a 1:1 mixture that includes Iodine and Gadolinium. Of course, other mixture ratios (e.g., up to 1:5 or more), another number of materials, and/or other materials are contemplated herein, and the mixture including Iodine and Gadolinium are shown for explanatory purposes.

Figure 4:
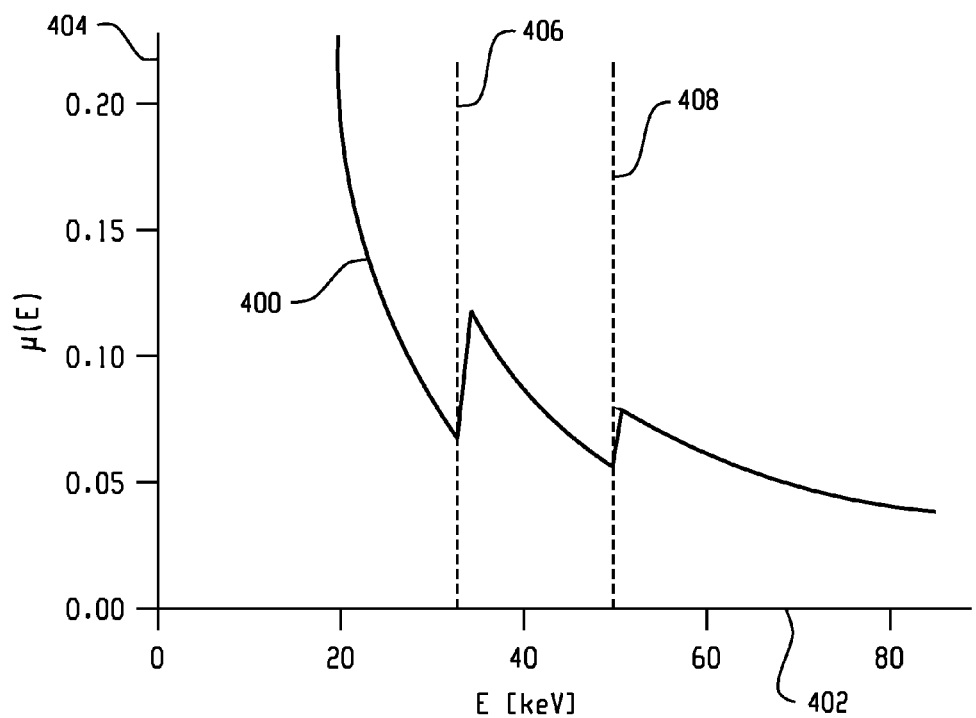
FIG. 4 illustrates an example multi K-edge attenuation curve.

In FIG. 4, the x-axis, axis 402, represents energy (E) in units of keV, and the y-axis, axis 404, represents attenuation ($\mu$) as a function of energy (E). The K-edge of Iodine (K-edge$\approx$33 keV) is shown at 406, and the K-edge of Gadolinium (K-edge$\approx$50 keV) is shown at 408. As such, the attenuation of the contrast agent can be characterized by two discontinuities at respective K-edge energies with fixed respective heights. If the stoichiometric ratio were different (not 1:1), for example, two units (e.g., atoms, etc.) of Iodine to one unit of Gadolinium, then a height-ratio of the K-edge 406 and 408 in FIG. 4 would be twice as high. As a consequence, the curve 400 can be used as a unique signature for a particular combination of elements.

Figure 5:
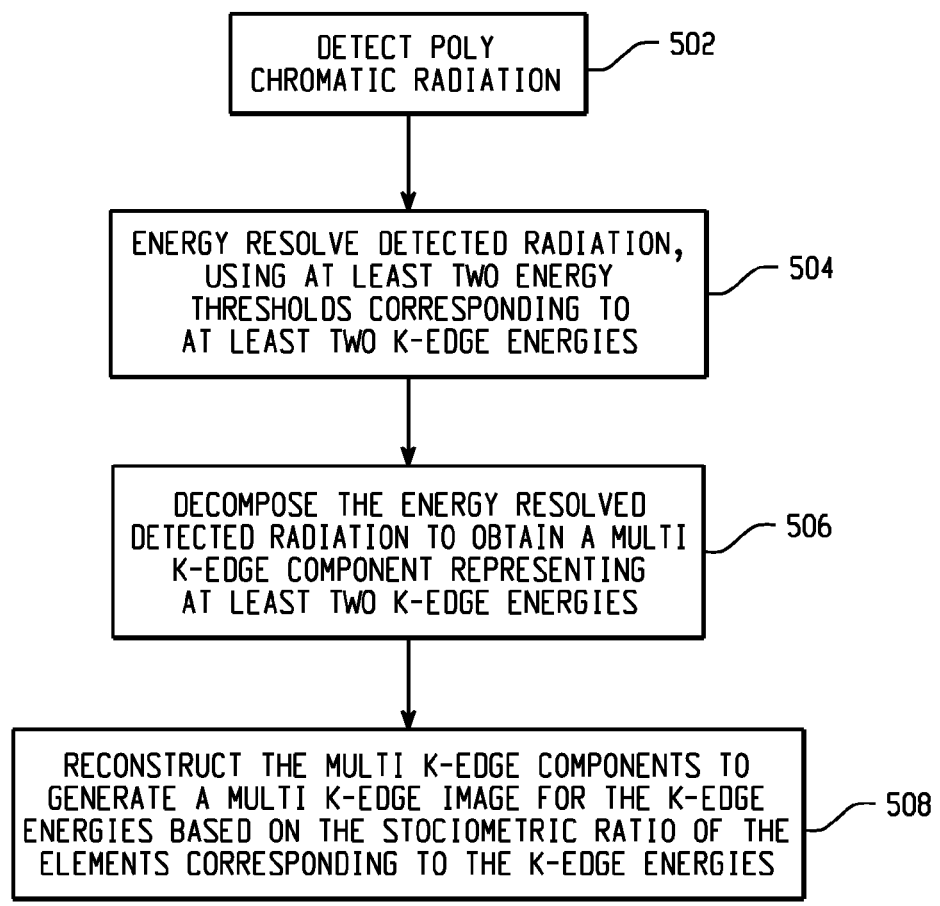
FIG. 5 illustrates a method.

FIG. 5 illustrates a multi K-edge component imaging method. At 502, poly-chromatic radiation emitted by a radiation source and traversing an examination region is detected. At 504, the detected radiation is energy-resolved and binned across different energy windows based on a plurality of threshold corresponding to different energies in which at least two of the thresholds are set in accordance with the K-edge energies of at least two elements in a contrast agent provided to a patient prior to scanning the patient. As discussed above, this may include four (4) energy thresholds in which two (2) of the thresholds are tuned to two different K-edge energies in accordance with the dual K-edge material contrast agent. At 506, the energy-resolved data is decomposed into constituent components, including a multi K-edge component representing two or more K-edge energies corresponding to the at least two elements in the contrast agent. At 508, at least the K-edge component is reconstructed using the stoichiometric ratio of the elements in the contrast agent to generate a multi K-edge component image.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention is claimed to be:

1. An imaging system, comprising:
   a radiation source that emits poly-chromatic radiation that traverses an examination region;
   a detector that detects radiation traversing the examination region and produces a signal indicative of the energy of a detected photon;
   an energy discriminator that energy resolves the signal based on a plurality of different energy thresholds, wherein at least two of the energy thresholds have values corresponding to at least two different K-edge energies of two different elements in a mixture disposed in the examination region;
   a signal decomposer that decomposes the energy-resolved signal into at least a multi K-edge component representing the at least two different K-edge energies; and
   a reconstructor that reconstructs the multi K-edge component to generate a multi K-edge image, representative of the different materials, based on a stoichiometric ratio of the two different elements in the mixture that is known and substantially constant.

2. The imaging system of claim 1, wherein the stoichiometric ratio is in a range of about 1:1 to about 1:5.

3. The imaging system of claim 1, wherein the stoichiometric ratio and the K-edge energies provide a unique fingerprint for the mixture of the two different elements.

4. The imaging system of claim 1, wherein the two different elements are part of a single contrast agent.

5. The imaging system of claim 1, wherein the signal decomposer further decomposes the energy-resolved signal into a Compton component and a photo-electric component.

6. The imaging system of claim 5, wherein the reconstructor reconstructs the Compton component and the photo-electric component to generate a Compton component image and a photo-electric component image.

7. The imaging system of claim 1, wherein the K-edge energies are within a range from about 25 keV to about 150 keV.

8. The imaging system of claim 1, wherein at least one of the K-edge energies is about 33 keV.

9. The imaging system of claim 1, wherein at least one of the K-edge energies is about 50 keV.

10. A method, comprising:
    detecting poly-chromatic radiation emitted by a radiation source that traverses an examination region;
    generating a signal indicative of the energy of a detected photon;
    energy-resolving the signal based on a plurality of different energy thresholds, wherein at least two of the energy thresholds have values corresponding to at least two different K-edge energies of two different elements of a mixture disposed in the examination region, wherein a stoichiometric ratio of the two different elements of the mixture is known;
    decomposing the energy-resolved signal into at least a multi K-edge component representing the at least two different K-edge energies; and
    reconstructing a multi K-edge image based on the multi K-edge component and the stoichiometric ratio to generate volumetric image data indicative of the two different elements.

11. The method of claim 10, wherein the stoichiometric ratio is substantially constant.

12. The method of claim 10, wherein the stoichiometric ratio is in a range of about 1:1 to about 1:5.

13. The method of claim 10, wherein the stoichiometric ratio and the K-edge energies uniquely characterize the attenuation behavior of the elements as a function of photon energy.

14. The method of claim 10, further including decomposing the energy-resolved signal into a Compton effect component and a photo-electric effect component.

15. The method of claim 10, further including reconstructing the Compton component and the photo-electric component to generate volumetric image data indicative of the Compton component and the photo-electric component.

16. The method of claim 10, wherein the mixture includes at least a third contrast element, and further including at least a third threshold corresponding to the third contrast element; decomposing the energy-resolved signal into at least a multi K-edge component representing the at least three different K-edge energies; and reconstructing a multi K-edge image based on the multi K-edge component and the stoichiometric ratio to generate volumetric image data indicative of the three different elements.

17. A non-transitory computer readable storage medium containing instructions which, when executed by a computer, cause the computer to perform the steps of:
    detecting poly-chromatic radiation traversing the examination region;
    producing a signal indicative of an energy of a detected photon;
    energy discriminating the signal based on a plurality of different energy thresholds, wherein at least two of the energy thresholds have values corresponding to at least two different K-edge energies of two different elements disposed in the examination region;
    decomposing the energy-resolved signal into a multi K-edge component representing the at least two different K-edge energies; and
    reconstructing the multi K-edge component based on a stoichiometric ratio of the two different elements in a contrast agent, wherein the stoichiometric ratio is known and substantially constant.

* * * * *